US008486628B2

(12) United States Patent
Loeffert et al.

(10) Patent No.: US 8,486,628 B2
(45) Date of Patent: Jul. 16, 2013

(54) METHOD OF NORMALIZED QUANTIFICATION OF NUCLEIC ACIDS USING ANCHOR OLIGONUCLEOTIDES AND ADAPTER OLIGONUCLEOTIDES

(75) Inventors: Dirk Loeffert, Duesseldorf (DE); Christian Korfhage, Langenfeld (DE); Holger Engel, Hilden (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 13/388,224

(22) PCT Filed: Jul. 30, 2010

(86) PCT No.: PCT/EP2010/004914
§ 371 (c)(1),
(2), (4) Date: Apr. 6, 2012

(87) PCT Pub. No.: WO2011/012330
PCT Pub. Date: Feb. 3, 2011

(65) Prior Publication Data
US 2012/0252014 A1 Oct. 4, 2012

(30) Foreign Application Priority Data
Jul. 31, 2009 (EP) .................................... 09167013

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC ......... 435/6.1; 435/6.12; 435/91.1; 435/91.2; 536/23.1; 536/24.3

(58) Field of Classification Search
USPC ............ 435/6.1, 6.12, 91.1, 91.12; 536/23.1, 536/24.3
See application file for complete search history.

(56) References Cited

U.S. PATENT DOCUMENTS

| 5,976,797 A | 11/1999 | Mitsuhashi |
| 2002/0132241 A1 | 9/2002 | Fan et al. |
| 2003/0068629 A1* | 4/2003 | Rothberg et al. ................ 435/6 |
| 2003/0099950 A1* | 5/2003 | Hanna ............... 435/6 |
| 2008/0057543 A1 | 3/2008 | Korfhage et al. |

FOREIGN PATENT DOCUMENTS

| DE | 10 2006 020885 | 11/2007 |
| WO | WO 99/43850 | 9/1999 |
| WO | WO 03/062389 | 7/2003 |
| WO | WO 2008/020008 | 2/2008 |

OTHER PUBLICATIONS

Miura et al, Absolute quantification of the budding yeast transcriptome by means of competitive PCR between genomic and complementary DNAs, 2008, BMC Genomics, 9:574, pp. 1-14.*
Wong, et al., "Real-time PCR for mRNA Quantitation" Biotechniques, Jul. 2005, vol. 39, No. 1, pp. 75-85.

* cited by examiner

*Primary Examiner* — Narayan Bhat
(74) *Attorney, Agent, or Firm* — Fanelli Haag & Kilger PLLC

(57) ABSTRACT

The present invention is related to normalized quantification of nucleic acids and to the normalization of quantities of nucleic acids in samples, e.g. mixtures of nucleic acids. The present invention relates to method for the normalization of the quantity of a nucleic acid to be quantified in a sample to the total quantity of nucleic acid in the sample; or to the total quantity of a specific class of nucleic acid in the sample.

21 Claims, 1 Drawing Sheet

US 8,486,628 B2

METHOD OF NORMALIZED QUANTIFICATION OF NUCLEIC ACIDS USING ANCHOR OLIGONUCLEOTIDES AND ADAPTER OLIGONUCLEOTIDES

This application is a National Stage of PCT/EP2010/004914, filed Jul. 30, 2010 which claims priority to European Application No. 09167013.3, filed Jul. 31, 2009, the disclosures of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on May 18, 2012, is named 05154US1.txt and is 1,762 bytes in size.

TECHNICAL FIELD OF THE INVENTION

The present invention is in the field of Biology and Chemistry. In particular, the invention is in the field of Molecular Biology. More particular, the invention is in the field of quantification of nucleic acids and real-time PCR. Furthermore, the invention is related to normalized quantification of nucleic acids and to the normalization of quantities of nucleic acids in samples, e.g. mixtures of nucleic acids.

BACKGROUND OF THE INVENTION

The quantification (quantitation) of specific nucleic acids in mixtures of nucleic acids is of importance in a number of applications in molecular biology, such as gene expression analysis or during purification of specific nucleic acids from a mixture of nucleic acids. In quantification methods, the concentrations and/or the relative or absolute amounts of specific nucleic acids in samples are determined. In particular, for the analysis of gene expression, for example for measuring mRNA levels in biological samples, a reproducible and comparative method is desired. For example, it is not always possible to obtain biological samples with comparable volume, amount of nucleic acid, cellular material or the like. Different samples can, for example, comprise RNA or DNA derived from different tissues, from different organisms or individuals, or cell culture samples that have been treated with different compounds.

In addition, sensitivity and selectivity of detection and quantification of nucleic acids in biological samples is of importance. For better comparison of the quantities of specific nucleic acids in two or more different (biological) samples or the comparison of the quantities of two or more different specific nucleic acids in a sample, a normalization of the quantities of the specific nucleic acids to the input nucleic acids or a specific class of input nucleic acid has to be performed. Quantities of specific nucleic acids can, e.g., be normalized by relating these quantities to an internal standard of the sample or to the overall, i.e. total, amount of nucleic acid or to the amount of a specific class of nucleic acid in the sample.

For conventional quantification of nucleic acids in (biological) samples, quantitative (real-time) PCR (qPCR) is widely used. For RNA, particularly mRNA, quantitative real-time reverse transcription PCR (RT-qPCR) is used in this field. Different approaches for the normalization of data obtained from quantitative PCR methods have been employed. Among them is the normalization of the quantities of specific mRNAs to the quantities of one or more mRNAs of different reference genes, e.g. housekeeping or maintenance genes, such as beta-actin, glyceraldehyde-3-phosphate dehydrogenase (GAPDH), hypoxanthine-guanine phosphoribosyl transferase (HPRT), or 28S or 18S ribosomal RNA. However, the expression levels of such normalizer genes have been shown to vary depending on experimental conditions, preparation and source (e.g. tissue or cell type) of the samples and therefore they are not reliably indicative for the input nucleic acids. It is therefore commonly required to test a range of different housekeeping genes in a laborious and error-prone procedure in order to identify those which do not change between samples under investigation.

Other approaches, for example, rely on the normalization to the total content of DNA and/or RNA or the total content of e.g. ribosomal RNA (rRNA). As the content of ribosomal RNA in biological cells and samples is also subject to variations depending on a variety of factors, normalization to rRNA is also less preferred. Methods relying on the normalization to e.g. total nucleic acid content, total RNA content or total content of genomic DNA are also limited, e.g. by variations in these contents or the quality of the nucleic acid samples. Normalization to alien or artificial molecules, e.g. in vitro transcripts, that have been incorporated into a sample (e.g. a cell extract or a sample derived from a tissue) is also not in all cases an adequate procedure, since they do not represent the nucleic acid (e.g. genomic DNA, RNA, mRNA) content in a cell.

Besides, for comparison of normalized data and reproducibility of the experimental procedures, thorough documentation of the applied experimental conditions is required. This is particularly relevant, when the quantities of the nucleic acid of interest and the normalizer nucleic acid are determined separately or using different methods.

Therefore, the technical problem underlying the present invention was to develop and to provide an improved, in particular a less laborious and error-prone, method for the normalization of quantities of nucleic acids.

SUMMARY OF THE INVENTION

The present invention provides (a) robust and improved method(s) for the normalization of the quantity of a (specific) nucleic acid (i.e. a "target nucleic acid") in a sample or in a plurality of samples to the total quantity of nucleic acid in the sample(s); or the total quantity of a specific class of nucleic acid in the sample(s). The present invention also relates to a kit for the normalization of the quantity of a (specific) nucleic acid (i.e. a "target nucleic acid") in a sample or in a plurality of samples to the total quantity of nucleic acid in the sample(s); or the total quantity of a specific class of nucleic acid in the sample(s).

In the context of the present invention, a specific class of nucleic acid may be, inter alia, RNA, DNA, cDNA (complementary DNA), LNA (locked nucleic acid), mRNA (messenger RNA), mtRNA (mitochondrial), rRNA (ribosomal RNA), tRNA (transfer RNA), nRNA (nuclear RNA), siRNA (short interfering RNA), snRNA (small nuclear RNA), snoRNA (small nucleolar RNA), scaRNA (Small Cajal Body specific RNA), microRNA, dsRNA (doubled-stranded RNA), ribozyme, riboswitch, viral RNA, dsDNA (double-stranded DNA), ssDNA (single-stranded DNA), plasmid DNA, cosmid DNA, chromosomal DNA, viral DNA, mtDNA (mitochondrial DNA), nDNA (nuclear DNA), snDNA (small nuclear DNA) or the like or any other class or sub-class of nucleic acid which is distinguishable from the bulk nucleic acid in a sample.

The means and methods of the present invention comprise the use of nucleic acid probes. A nucleic acid probe according to the present invention is an oligonucleotide, nucleic acid or a fragment thereof, which is substantially complementary to a specific nucleic acid sequence.

In general, the present invention relates to method for the normalization of the quantity of a nucleic acid to be quantified in a sample to
  (i) the total quantity of nucleic acid in the sample; or to
  (ii) the total quantity of a specific class of nucleic acid in the sample,
comprising the steps of
  a) providing a sample containing a nucleic acid to be quantified;
  b) adding a first nucleic acid probe to the sample under conditions allowing for hybridization of at least a terminal region of said first nucleic acid probe to specific binding sites of nucleic acid in the sample such that double-stranded nucleic acids are created, wherein said first nucleic acid probe comprises at least one primer binding site, a probe binding site, and an anchor oligonucleotide binding site;
  c) adding an anchor oligonucleotide under conditions allowing for hybridization to the anchor oligonucleotide binding site of the first nucleic acid probe so that a 5' sequence of the anchor oligonucleotide is not hybridized to the first nucleic acid probe;
  d) elongating the nucleic acid at its 3'end, wherein said first nucleic acid probe serves as template until the region is reached where said anchor oligonucleotide is hybridized to the first nucleic acid probe whereon the anchor oligonucleotide serves as a template for further elongation;
  e) quantifying the total amount of nucleic acid in the sample or the total amount of the specific class of nucleic acid in the sample using a second probe substantially complementary to a region of the DNA transcribed from said first nucleic acid probe and anchor oligonucleotide;
  f) quantifying the nucleic acid to be quantified using optionally a third probe whose sequence is substantially identical to a defined region of the nucleic acid to be quantified; and
  g) normalizing the quantity of the nucleic acid to be quantified by determining the ratio of the quantity of the nucleic acid to be quantified to the total quantity of nucleic acid in the sample or the total quantity of the specific class of nucleic acid in the sample.

The present invention also relates to a kit for the normalized quantification of nucleic acids in a sample, wherein the kit comprises one or more first nucleic acid probes substantially complementary to defined regions of nucleic acid or a specific class of nucleic acids in the sample, wherein the first nucleic acid probe comprises one or more primer binding sites and a probe binding site; and a second nucleic acid probe substantially complementary to said probe binding site on said first nucleic acid probe.

DETAILED DESCRIPTION OF THE INVENTION

The present invention provides a method for the normalization of the quantity of a nucleic acid to be quantified in a sample to
the total quantity of nucleic acid in the sample; or to
the total quantity of a specific class of nucleic acid in the sample,
comprising the steps of
providing a sample containing a nucleic acid to be quantified;
adding a first nucleic acid probe to the sample under conditions allowing for hybridization of at least a terminal region of said first nucleic acid probe to specific binding sites of nucleic acid in the sample such that double-stranded nucleic acids are created, wherein said first nucleic acid probe comprises at least one primer binding site, a probe binding site, and an anchor oligonucleotide binding site;
adding an anchor oligonucleotide under conditions allowing for hybridization to the anchor oligonucleotide binding site of the first nucleic acid probe so that a 5' sequence of the anchor oligonucleotide is not hybridized to the first nucleic acid probe;
elongating the nucleic acid at its 3'end, wherein said first nucleic acid probe serves as template until the region is reached where said anchor oligonucleotide is hybridized to the first nucleic acid probe whereon the anchor oligonucleotide serves as a template for further elongation;
quantifying the total amount of nucleic acid in the sample or the total amount of the specific class of nucleic acid in the sample using a second probe substantially complementary to a region of the DNA transcribed from said first nucleic acid probe and anchor oligonucleotide;
quantifying the nucleic acid to be quantified using optionally a third probe whose sequence is substantially identical to a defined region of the nucleic acid to be quantified; and
normalizing the quantity of the nucleic acid to be quantified by determining the ratio of the quantity of the nucleic acid to be quantified to the total quantity of nucleic acid in the sample or the total quantity of the specific class of nucleic acid in the sample.

The "total quantity of nucleic acid in the sample" or the "total quantity of a specific class of nucleic acid in the sample" refer to the reference quantities (reference nucleic acid) for normalization of the quantity of the nucleic acid to be quantified.

In particular embodiments of the invention the nucleic acid to be quantified is RNA and the specific class of nucleic acid is RNA.

A sample contains at least nucleic acid molecules comprising the nucleic acid to be quantified. The nucleic acids can be embedded in cells or organisms but can also be present in a cell free system. A sample may be a fluid, a lysate, solid matrix or anything else that contains nucleic acid molecules.

A nucleic acid in the context of the present invention relates to desoxyribo nucleic acid (DNA), ribo nucleic acid (RNA) or peptide nucleic acid (PNA). DNA and RNA are naturally occurring in organisms, however, they may also exist outside living organisms or may be added to organisms. The nucleic acid may be of any origin, e.g. viral, bacterial, archae-bacterial, fungal, ribosomal, eukaryotic or prokaryotic. It may be nucleic acid from any biological sample and any organism, tissue, cell or sub-cellular compartment. It may e.g. be nucleic acid from a plant, a fungus, an animal, and particularly human nucleic acid. The nucleic acid may be pre-treated before quantification, e.g. by isolation, purification or modification. Also artificial nucleic acid may be quantified. The length of the nucleic acids may vary. The nucleic acids may be modified, e.g. may comprise one or more modified nucleobases or modified sugar moieties (e.g. comprising methoxy groups). The backbone of the nucleic acid may comprise one or more peptide bonds as in peptide nucleic acid (PNA). The nucleic acid may comprise base analoga such as non-purine or non-pyrimidine analoga or nucleotide analoga. It may also comprise additional attachments such as proteins, peptides and/or or amino acids.

The "total quantity of nucleic acid in the sample" or the "total quantity of a specific class of nucleic acid in the sample" relate to nucleic acid having 3' ends that can be enlongated by a polymerase. Preferably, these nucleic acids or classes of nucleic acids are DNA or RNA, most preferably mRNA or cDNA.

The nucleic acid to be quantified is preferably a RNA or a DNA, most preferably a specific mRNA or cDNA.

In a particular embodiment of the invention, the DNA to be quantified is DNA selected from the group consisting of cDNA, dsDNA, ssDNA, plasmid DNA, cosmid DNA, chromosomal DNA, viral DNA and mtDNA and the total quantity of DNA is selected from the group consisting of the total quantity of DNA, the total quantity of cDNA, the total quantity of dsDNA, the total quantity of ssDNA, the total quantity of plasmid DNA, the total quantity of cosmid DNA, the total quantity of chromosomal DNA, the total quantity of viral DNA and the total quantity of mtDNA.

In another particular embodiment, the RNA to be quantified is RNA selected from the group consisting of mRNA, rRNA, tRNA, nRNA, siRNA, snRNA, snoRNA, scaRNA, microRNA, dsRNA, ribozyme, riboswitch and viral RNA and the total quantity of RNA is selected from the group consisting of the total quantity of RNA, the total quantity of mRNA, the total quantity of rRNA, the total quantity of tRNA, the total quantity of nRNA, the total quantity of siRNA, the total quantity of snRNA, the total quantity of snoRNA, the total quantity of scaRNA, the total quantity of microRNA, the total quantity of dsRNA, the total quantity of ribozyme, the total quantity of riboswitch, the total quantity of viral RNA.

The first nucleic acid probe ("adapter nucleic acid") herein is a nucleic acid probe comprising a terminal sequence substantially complementary to a specific binding sequence of nucleic acid (or of nucleic acid of a specific class of nucleic acid). Preferably this complementary sequence is at the 3' end of the first nucleic acid probe and the binding sequence is at the 3' end of the nucleic acid. The first nucleic acid probe comprises a binding site for an anchor oligonucleotide and optionally further probe or primer binding sites.

A skilled person knows how to choose the length and sequence of the probes and primers depending on the reaction temperature of the elongation reaction, on the particular enzyme(s) used (e.g. thermostable polymerase, reverse transcriptase) and on the sequence of the respective binding partners.

The anchor oligonucleotide ("anchor probe") comprises a sequence that binds (hybridizes) to the anchor oligonucleotide binding site on the first nucleic acid, i.e. that is substantially complementary to the sequence of the binding site. Additionally, the anchor oligonucleotide comprises 5' of the binding site a tag sequence complementary to a binding sequence for a second nucleic acid probe and optionally further probe and/or primer binding sites. The tag sequence and the adapter oligonucleotide binding sequence are chosen such that they do not appear in the nucleic acid to be quantified or the reference nucleic acid.

The second nucleic acid probe comprises a sequence complementary to the elongated sequence for which the 5' sequence of the anchor served as a template, i.e. the anchor oligonucleotide and the second oligonucleotide comprise a stretch of identical sequences.

The third nucleic acid probe comprises a sequence that is substantially complementary to a sequence of the nucleic acid to be quantified.

The enzyme having reverse transcriptase activity in the context of the invention may be of different origin, including viral, bacteria, Archae-bacteria and eukaryotic origin, especially originating from thermostable organisms. This includes enzymes originating from introns, retrotransposons or retroviruses. An enzyme with reverse transcriptase activity in the context of the invention is an enzyme which is able to add to the 3' end of a desoxyribonucleic acid or a ribonucleic acid, hybridized to a complementary desoxyribonucleic acid or a ribonucleic acid or vice versa, one or more desoxyribonucleotides at suitable reaction conditions, e.g. buffer conditions, complementary to said desoxyribonucleic acid or a ribonucleic acid. This includes enzyme, that intrinsically have reverse transcriptase, but also enzymes that were evolved or mutated in their gene sequence to gain such function or that gain such function by adjusting buffer or other reaction parameters.

Preferably, the enzyme having reverse transcriptase activity in the context of the invention is selected from the group comprising HIV reverse transcriptase, M-MLV reverse transcriptase, EAIV reverse transcriptase, AMV reverse transcriptase, *Thermus thermophilus* DNA Polymerase I, M-MLV RNase H, Superscript, Superscript II, Superscript III, Monstersript (Epicentre), Omniscript, Sensiscript Reverse Transcriptase (Qiagen), ThermoScript and Thermo-X (both Invitrogen). The enzyme may also have increased fidelity like e.g. AccuScript reverse Transcriptase (Stratagene). A skilled person knows that one or more suitable enzyme with reverse transcriptase activity can be mixed to gain optimized conditions or novel features. This may include amongst others mixtures of e.g. a mesophilic and a thermophilic enzymes, or an enzyme having RNase H activity and an enzyme being RNase H negative, or an enzyme with increased fidelity and an thermophilic enzyme. Numerous other combinations are possible based on the list of preferred enzymes having reverse transcriptase activity in the scope of the invention.

A "primer" herein refers to an oligonucleotide comprising a sequence that is complementary to a nucleic acid to be transcribed ("template"). During replication polymerases attach nucleotides to the 3' end of the primer complementary to the respective nucleotides of the template.

Preferably, the RNA to be quantified is mRNA and the specific class of nucleic acid is mRNA.

In preferred embodiments of the invention the specific binding site is a poly-A sequence or a poly-A tail.

In other embodiments of the invention the nucleic acid to be quantified is DNA and the specific class of nucleic acid is DNA.

Preferably, the DNA to be quantified is cDNA and the specific class of nucleic acid is cDNA.

Particularly, the specific binding site is specific for mRNA or is a poly-A sequence or a poly-A tail. The poly-A tail can be as naturally occurring in the sample RNA. In case the RNA does not contain a poly-A tail, experimental procedures can be employed to add a suitable homopolymeric tail to the 3' end of the RNA. Such tail can be composed of A, C, G, or U Bases or suitable base analogues. Addition of such tail can be performed chemically or enzymatically. Enzymes can be selected from the classes of poly-A polymerase, terminal transferase, ligase, or other suitable enzyme catalyzing addition or linkage of nucleotides to the 3' end of a nucleic acid.

Preferably, the first nucleic acid probe is DNA or RNA.

In some embodiments of the invention quantification comprises a nucleic acid amplification reaction such as the non-isothermal amplification methods polymerase chain reaction (PCR), particularly quantitative real-time PCR or isothermal amplification methods such as NASBA (nucleic acids sequence based amplification), TMA (Transcription mediated amplification), 3SR (self-sustained sequence amplification), SDA (Strand displacement amplification), HDA (helicase dependent amplification, with heat-labile or heat-stabile enzymes), RPA (recombinase polymerase amplification), LAMP (Loop-mediated amplification); or SMAP (SMart Amplification Process) These technologies make use of a couple of different enzymes, proteins, primers and accessory molecules that are well known for persons skilled in the art. The polymerases include polymerases selected from the group comprising *Thermus thermophilus* (Tth) DNA polymerase, *Thermus acquaticus* (Taq) DNA polymerase, *Thermotoga maritima* (Tma) DNA polymerase, *Thermococcus litoralis* (Tli) DNA polymerase, *Pyrococcus furiosus* (Pfu) DNA polymerase, *Pyrococcus woesei* (Pwo) DNA polymerase, *Pyrococcus kodakaraensis* KOD DNA polymerase, *Thermus filiformis* (Tfi) DNA polymerase, *Sulfolobus solfataricus* Dpo4 DNA polymerase, *Thermus pacificus* (Tpac) DNA polymerase, *Thermus eggertsonii* (Teg) DNA polymerase and *Thermus flavus* (Tfl) DNA polymerase and the polymerases of phages e.g. Phi29-phage, Phi29 like phages such as Cp-1, PRD-1, Phi 15, Phi 21, PZE, PZA, Nf, M2Y, B103, SF5, GA-1, Cp-5, Cp-7, PR4, PR5, PR722, or L 17. The polymerases include also polymerase form other organism such as from *E. coli*, T4, T7. Other additional proteins may improve the methods, for example helicases, single-stranded binding proteins, or other DNA-binding proteins, and recombinases.

In preferred embodiments of the invention said first nucleic acid probe hybridizes in such a fashion to said specific binding site that it is positioned at or close to the 5' end of said poly-A sequence or poly-A tail, i.e. within 5 nucleotides, 10 nucleotides, 20 nucleotides to the 5' end. Preferably said first nucleic acid probe hybridizes in such a fashion to said specific binding site that it is positioned at the 5' end of said poly-A sequence or poly-A tail, wherein at herein means within 0, 1, 2, 3, 5, 10 nucleotides to the 5' end.

The quantifying steps may in some embodiments comprise a method selected from the group consisting of gel electrophoresis, capillary electrophoresis, labelling reactions with subsequent detection measures and quantitative real-time PCR. Preferably, quantification comprises quantitative real-time PCR or quantitative real-time reverse transcription PCR. In preferred embodiments of the invention, the quantification step(s) comprise(s) (i) the reverse transcription of RNA (e.g. mRNA) into DNA (e.g. cDNA) using a RNA-dependent DNA polymerase (i.e. a reverse transcriptase), (ii) the amplification of the DNA produced by reverse transcription using PCR, and (iii) the detection and quantification of the amplification products in real time.

Some embodiments of the invention additionally comprise a step of contacting the RNA in the sample with a reverse transcriptase subsequent to the ligation step under conditions allowing for the reverse transcription of RNA or the specific class of RNA in the sample.

In some embodiments of the invention reverse transcribing and quantifying are performed in the same reaction container.

The reverse transcriptase may be a polymerase also used for amplification during the quantification steps.

Selective primers or random primers may be used in quantitative real-time PCR to quantify the cDNA of the first nucleic acid probe. Preferably selective primers are used in real-time PCR. In a more preferred embodiment, selective primers allowing amplification of the cDNA generated from the first nucleic probe, optionally an additional nucleic acid probe are used. Optionally, one or more additional selective primer sets are present in the reaction, optionally an additional nucleic acid probe, allowing co-amplification (multiplex amplification) of one more target nucleic acid species to be quantified.

In some embodiments of the invention, the quantity of the nucleic acid to be quantified and the total quantity of nucleic acid or the total quantity of the specific class of nucleic acid are determined at the same time.

The second and third nucleic acid probe are labelled with one or more fluorescent dye(s) and wherein the quantifying steps comprise detecting fluorescence signals in the sample.

Preferably, the second and third nucleic acid probes are fluorescently labelled probes selected from the group consisting of hybridization probe, hydrolysis probe and hairpin probe.

Particularly, the fluorescently labelled probes are labelled with a dye selected from the group consisting of FAM, VIC, NED, Fluorescein, FITC, IRD-700/800, CY3, CY5, CY3.5, CY5.5, HEX, TET, TAMRA, JOE, ROX, BODIPY TMR, Oregon Green, Rhodamine Green, Rhodamine Red, Texas Red, Yakima Yellow, Alexa Fluor and PET.

In particular, the hybridization probe is a LightCycler probe (Roche) or the hydrolysis probe is a TaqMan probe (Roche). In other embodiments the hairpin probe is selected from the group consisting of molecular beacon, Scorpion primer, Sunrise primer, LUX primer and Amplifluor primer.

In some embodiments, the means and methods according to the present invention are used for the normalization of gene expression levels.

In some embodiments of the present invention additionally a pre-quantified nucleic acid is added to the sample and the quantity of said pre-quantified nucleic acid is determined in the quantifying steps. Preferably, the pre-quantified nucleic acid is a mRNA.

Preferably, the quantities of two or more nucleic acids to be quantified are normalized simultaneously, i.e. at the same time.

The present invention also relates to a kit for performing the method of any one of the above mentioned methods, wherein the kit comprises: (a) one or more first nucleic acid probes substantially complementary to defined regions of nucleic acid or a specific class of nucleic acids in the sample, wherein the first nucleic acid probe comprises one or more primer binding sites and a probe binding site; and (b) an adapter oligonucleotide substantially complementary to said probe binding site on said first nucleic acid probe.

Thus, the present invention relates to a kit for the normalized quantification of nucleic acids in a sample, wherein the kit comprises: (a) one or more first nucleic acid probes substantially complementary to defined regions of nucleic acid or a specific class of nucleic acids in the sample, wherein the first nucleic acid probe comprises one or more primer binding sites and a probe binding site; and (b) an second nucleic acid probe substantially complementary to said probe binding site on said first nucleic acid probe.

The kit may preferably be a comprising:

an adapter oligonucleotide substantially complementary to defined regions of nucleic acid or a specific class of nucleic acids in the sample, wherein the adapter oligonucleotide comprises one or more primer binding sites and a probe binding site; and an anchor oligonucleotide substantially complementary to said probe binding site on said adapter oligonucleotide, wherein said anchor oligonucleotide comprises 5' of the binding sequence to the adapter oligonucleotide a tag sequence.

In preferred embodiments of the invention, the kit additionally comprises a polymerase. The kit may additionally also comprise a nucleotide mixture and (a) reaction buffer(s). In some embodiments the kit additionally comprises a reverse transcriptase.

In particular embodiments, the kit additionally comprises one or more pre-quantified calibrator nucleic acids, a set of primers for the amplification of said calibrator nucleic acids and a first nucleic acid probe substantially complementary to a sequence on said pre-quantified nucleic acid.

The kit may additionally comprise primers substantially complementary to the first nucleic acid probe (adapter oligonucleotide)

the tag sequence of the anchor oligonucleotide and/or a sequence substantially complementary to the tag sequence or parts of the tag sequence of the anchor oligonucleotide.

The kit may also additionally comprise a second and/or third nucleic acid probe, wherein the second nucleic acid probe is substantially complementary to a sequence substantially complementary to the tag sequence or parts of the tag sequence of the anchor oligonucleotide and the third nucleic acid probe is substantially complementary to a sequence of the nucleic acid to quantified.

In some embodiments, one ore more of the components are premixed in the same reaction container.

As indicated herein above, for the analysis of gene expression, the quantification of mRNA in samples can be performed using quantitative real-time reverse transcription PCR (RT-qPCR). RT-qPCR methods employ a combination of three steps: (i) the reverse transcription of the mRNA into cDNA using a RNA-dependent DNA polymerase (i.e. a reverse transcriptase), (ii) the amplification of cDNA using PCR, and (iii) the detection and quantification of the amplification products in real time. For reverse transcription and PCR-based amplification, dNTPs ("nucleotide mixture") need to be present in the reaction buffer. A nucleotide mixture according to the present invention is a mixture of dNTPs, i.e. a mixture of dATP, dCTP, dGTP and dTTP/dUTP suitable for the use in PCR. For particular embodiments of the present invention the relative amounts of these dNTPs may be adapted according to the particular nucleotide content of the template nucleic acids. The RT-qPCR steps can either be performed in a single-stage process or in a two-stage process. In the first case, reverse transcription and PCR-based amplification are performed in the same reaction container, e.g. by utilizing a DNA polymerase which has intrinsic reverse transcription functionality, like *Thermus thermophilus* (Tth) polymerase. In a two-stage setup the steps of reverse transcribing the RNA and amplifying the DNA are performed separately, e.g. in different reaction containers. The steps of the methods according to the present invention may be conducted in suitable reaction buffers, e.g. comprising salts such as magnesium ions. As already stated, the different steps may or may not be conducted in the same buffers and reaction containers. In contrast to RT-qPCR, in qPCR no reverse transcription is performed, therefore it is a quantification method for DNA rather than for RNA.

The reverse transcription of (m)RNA in RT-qPCR and the amplification of (c)DNA in qPCR and RT-qPCR need to be primed by oligonucleotides ("primers"). In the case of mRNA quantification with RT-qPCR, mRNA specific oligonucleotides can be used, e.g. oligo-dT primers that hybridize to the poly-A-tail of mRNA. However, also random primers of varying lengths can be utilized.

Moreover, standard quantitative real-time PCR protocols and kits can be adapted or amended for the means and methods according to the present invention.

As mentioned above, real-time PCR (also designated herein as quantitative PCR or quantitative real-time PCR (qPCR)) is a method to simultaneously amplify and quantify nucleic acids using a polymerase chain reaction (PCR). Quantitative real-time reverse transcription PCR (RT-qPCR) is a quantitative real-time PCR method further comprising a reverse transcription of RNA into DNA, e.g. mRNA into cDNA. In qPCR and RT-qPCR methods, the amplified nucleic acid is quantified as it accumulates. Typically, fluorescent dyes that intercalate with double-stranded DNA (e.g. ethidiumbromide or SYBR® Green I) or modified nucleic acid probes ("reporter probes") that fluoresce when hybridized with a complementary nucleic acid (e.g. the accumulating DNA) are used for quantification in qPCR based methods. Particularly, fluorogenic primers, hybridization probes (e.g. LightCycler probes (Roche)), hydrolysis probes (e.g. TaqMan probes (Roche)), or hairpin probes, such as molecular beacons, Scorpion primers (DxS), Sunrise primers (Oncor), LUX primers (Invitrogen), Amplifluor primers (Intergen) or the like can be used as reporter probes. In accordance with the present invention, fluorogenic primers or probes may for example be primers or probes to which fluorescence dyes have been attached, e.g. covalently attached. Such fluorescence dyes may for example be FAM (5- or 6-carboxyfluorescein), VIC, NED, Fluorescein, FITC, IRD-700/800, CY3, CY5, CY3.5, CY5.5, HEX, TET, TAMRA, JOE, ROX, BODIPY TMR, Oregon Green, Rhodamine Green, Rhodamine Red, Texas Red, Yakima Yellow, Alexa Fluor, PET and the like. Particular reporter probes may additionally comprise fluorescence quenchers.

In an illustrative but not liming embodiment of the invention, a specific mRNA in a sample is to be quantified and its quantity is to be normalized to the overall mRNA quantity in the sample. The overall quantity of mRNA is quantified using an adapter oligonucleotide ("first nucleic acid probe" herein), an anchor oligonucleotide and a second nucleic acid probe. The quantity of the specific mRNA is quantified using a third nucleic acid probe. The quantification in this embodiment is performed using a quantitative reverse transcription real-time PCR, wherein the first nucleic acid probe comprises a sequence complementary to the poly-A tail of mRNA. The first nucleic acid probe serves as an adapter for the binding of the anchor oligonucleotide probe. The first nucleic acid probe serves as a template for the elongation of the mRNA until the region is reached where the anchor oligonucleotide is bound to the first nucleic acid probes, from there on the 5' sequence of the nucleic acid probe serves as a template. This leads to an elongated mRNA with introduced primer and/or probe sequences. Upon replication, the introduced primer and/or probe binding sites serve for the quantification using real-time PCR with labelled primers and/or probes. The specific mRNA to be quantified is quantified using labelled probes and/or primers.

The present invention also relates to the use of the methods of the invention or the kit of the invention for the normalization of the quantity of a specific nucleic acid to the quantity of a reference nucleic acid.

Furthermore, the present invention also relates to the use of the methods of the invention or the kit of the invention gene expression analysis.

In the context of the present invention mRNA may preferably be poly-adenylated messenger RNA as naturally occurring from different species. mRNA may also be any mRNA, naturally with or without poly-A tail, wherein a poly-nucleotide tail is added in vitro by a suitable method, e.g. an enzyme, preferred a poly-A-polymerase.

1-x describes the lengths of the poly-nucleotide-tail, as naturally occurring or added in vitro. Suitable length varies from 1 to 1000 s.

A[A]AAAA describes the poly-nucleotide-tail, which can be the naturally occurring poly-A-tail, or a poly-nucleotide tail added in vitro by a suitable method. 3' OH is available to allow enzymatic extension.

The adapter nucleic acid is a nucleic acid oligonucleotide, RNA or DNA or an analogous form thereof It is comprised of an element hybridizing to the poly-nucleotide-tail, which can be the naturally occurring poly-A-tail, under the given reaction conditions. In case the mRNA carries a poly-A-tail, the hybridizing element is preferred to be comprised of the bases complementary to A, namely U Bases or T Bases. In a preferred embodiment, the lengths of the hybridizing element is between 1 and 150, more preferred between 2 and 100, most preferred between 4 and 80 nucleotides. Useful lengths may be limited by available production or synthesis technologies.

The adapter nucleic acid comprises the adapter sequence. The adapter sequence is preferably selected to have sufficient lengths to allow specific detection of the cDNA in a detection method, generated using this sequence as template. One preferred detection method is PCR. In this case, the adapter sequence harbours sufficient lengths for at least one PCR primer, and optionally for one or more sequence specific probes. The 3' OH group of this adapter nucleic acid can be blocked to prevent extension or can be free, to allow cDNA synthesis. Appropriate methods to block the 3' OH are standard methods and known in the art. Suitable methods may be a 3' phosphate group, inverse base, aliphatic linker, amino modifier, or others.

The enzyme is at least one enzyme allowing cDNA synthesis using the poly-nucleotide tail as primer and the adapter nucleic acid as template. Different enzymes are possible dependent on the type of nucleic acids used in the poly-A-Tail or the adapter nucleic. It may originate from mesophilic or thermophilic organisms, providing activity in a temperature range from 5° C. to 100° C., preferably from 10° C. to 80° C., most preferably from 15° C. to 75° C.

dNTPs are desoxynucleotide triphosphates required for DNA synthesis. The mixture may optionally contain modified nucleotides or labelled nucleotides or nucleotide analoga.

A "buffer" in the context of the present invention is a suitable buffer solution providing one or more buffer substances, a suitable pH, cations, cofactors like $Mg^{++}$, providing reaction conditions for the cDNA synthesis at the given reaction temperature and the given one or more enzymes.

EXAMPLES

Example 1

Generation and Detection of cDNA from Using an Adapter Oligonucleotide and an Anchor Oligonucleotide and Detection of cDNA in Real-time PCR In this experiment the feasibility of the concept shown in FIG. 1 shall be demonstrated. The reactions have been composed as shown in table 1 and carried out with the protocol shown in table 2. The reaction volume depends on the amount of RNA which should be detected (see table 1). For this purpose the reagents of table 3 were used. RNA sample was total RNA isolated using standard procedures (Rneasy Kit, Qiagen) from Hela cells. As a control for background signal, a negative control reaction cDNA synthesis reaction with 1 µg total Hela RNA and all components except the adapter and anchor Nucleic Acid.

TABLE 1

Setup for cDNA synthesis using an adapter oligonucleotide and an anchor oligonucleotide

| Component | Final concentration |
| --- | --- |
| Buffer RT, 10x | 1x |
| RNAse Inhibitor, 40 Units/µl | 2 Units/µl |
| DNA Polymerization Mix 10 mM dNTP | 0.5 mM |
| Omniscript Reverse Transkriptase, 4 Units/µl | 0.2 Units/µl |
| Adapter Nucleic Acid | 0.2 µM |
| Anchor Oligo | 1 µM |
| RNAse free water | variable |
| RNA Sample concentration | Total RNA concentraton: 0.2-2.0 ng/µl) |
| Reaction volume | 500 µl |

TABLE 2

Protocol for cDNA synthesis using an adapter oligonucleotide and an anchor oligonucleotide

| Reverse transcription (RT) | 37° C. for 45 minutes |
| --- | --- |
| RT inactivation | 95° C. for 5 minutes |
| | 4° C. Hold |

TABLE 3

Reagents for cDNA synthesis

| | |
| --- | --- |
| Buffer RT, 10x | Components of QIAGEN-Omniscript RT |
| Omniscript Reverse Transkriptase, 4 Units/µl | Kit Maternial No. 205111 |
| RNAse free water | |

TABLE 3-continued

Reagents for cDNA synthesis

| | |
|---|---|
| RNAse Inhibitor, 40 Units/µl | Promega Material No. N251B |
| 10 mM dNTP | Amersham Material No. 27-2074-60 |
| Anchor Oligonucleotide | Synthetic DNA Oligonucleotide<br>5'-CACATCAGGATTCCTAGGACCAATATCACTCACC-3'P<br>(SEQ ID NO: 1) |
| Adapter Nucleic Acid | Synthetic RNA Oligonucleotide:<br>GGT GAG TGA TTG GAG GGT TGA GCA CAT CAG<br>AGC CCT GCG ATG AGT CTG TCG TCG TCT CGT<br>TCC AUU UUU UUU UUU UUU UU-3'NH2<br>(SEQ ID NO: 2) |

After reverse transcription, the generated cDNA was then used as template in SYBR Green based real-time PCR, in order to analyse if a correlation between the observed Ct-Value in real-time PCR and the amount of RNA used in cDNA synthesis can be observed.

To this end, after inactivation of the RT enzyme (see table 2: 5 minutes at 95° C.) 5 µl of the cDNA synthesis reaction was applied as template to each reaction in the following real-time PCR. The detection in real-time PCR was carried out with SYBR Green chemistry. Table 5 shows the setup for a SYBR Green real-time PCR reaction. The PCR reaction was prepared with the components from table 4. Duplicate reaction for each condition were performed. Afterwards the cycling shown in table 6 was performed. Real-time PCR was carried out on a Applied Biosystems 7500 Real-time PCR System. Subsequently the data were analyzed with the appropriate software (SDS software). The results are shown in table 7.

From these results it becomes obvious, that a correlation between the observed Ct value in real-time PCR and the amount of input RNA in the cDNA synthesis reaction can be observed. As shown in Table 7, the Ct difference, referred to as delta Ct, between the amount of input RNA and the Ct value almost perfectly fits the theoretical Ct differences. For the 2-fold difference between 1 µg and 500 ng a Ct difference of 1.08 was observed. Taking into account the PCR efficiency of the given PCR assay at the given conditions of close to 100% (data not shown) and the inaccuracy of measurement of the real-time PCR instrument, these values almost exactly fit the optimal theoretical difference of 1.0. For the 5-fold difference between 500 ng and 100 ng, a Ct difference of 2.36 was observed. The theoretical difference for the 5-fold difference with the given 100% PCR efficiency is 2.32. Hence, a very good correlation between amount of input RNA and the Ct value was observed in the example, demonstrating that the system is suitable for quantify total nucleic acid, e.g. RNA in a sample and use these values for normalization of the total amount of nucleic acid, e.g. RNA in a sample.

The negative control reaction (5 µl from a cDNA synthesis reaction with 1 µg total Hela RNA and all components except the adapter and anchor Nucleic Acid) remained negative in PCR, as noted by "undetermined" Ct value after 45 cycles, demonstrating the high specificity of the reaction.

Taken together, the concept shown in FIG. 1 allows quantification and subsequently normalization of a nucleic acid, e.g. RNA in a sample.

TABLE 4

Components and material numbers for SYBR Green Real-time PCR setup

| | |
|---|---|
| QuantiTect SYBR Green PCR Mastermix 2x | Components of QIAGEN-QuantiTect SYBR Green PCR Kit Material No. 204143 |
| RNAse free water | |
| HUM-Uni | AAC GAG ACG ACG ACA GAC (SEQ ID NO: 3) |
| HBSF 1 | CACATCAGGATTCCTAGGACC (SEQ ID NO: 4) |

TABLE 5

Setup for Real-Time PCR with SYBR Green

| Components | Final concentration |
|---|---|
| QuantiTect SYBR Green PCR Mastermix, 2x | 1x |
| HUM-Uni primer | 0.4 µM |
| HBSF 1 primer | 0.4 µM |
| RNAse free water | to 20 µl per reaction |
| Template (from cDNA synthesis reaction) | 5 µl reaction |
| Final reaction volume | 25 µl |

TABLE 6

Protocol for Real-time PCR with SYBR Green

| | | |
|---|---|---|
| PCR initial reactivation | 95° C. for 15 minutes | |
| Denaturing | 95° C. for 15 seconds | 45x |
| Annealing | 55° C. for 30 seconds | |
| Extension (Data acquisition) | 70° C. for 30 seconds | |
| Followed by dissociation stage (Melting curve analysis) | | |

TABLE 7

Results of SYBR Green Real-time PCR

| Amount of RNA used in cDNA synthesis | Template in Real-time PCR | Ct | Mean Ct of duplicates | Delta Ct | Theoretical delta Ct |
|---|---|---|---|---|---|
| 1 µg Hela RNA | 5 µl of cDNA synthesis | 34.24<br>34.64 | 34.44 | | |
| 500 ng Hela RNA | 5 µl of cDNA synthesis | 35.78<br>35.26 | 35.52 | 1.08 | 1.0 |
| 100 ng Hela RNA | 5 µl of cDNA synthesis | 37.71<br>38.05 | 37.88 | 2.36 | 2.32 |
| Negative Control (1 µg Hela RNA without Adapter + Anchor Nucleic Acid) | 5 µl of cDNA synthesis | Undetermined | — | — | — |

DESCRIPTION OF DRAWINGS

FIG. 1 discloses 'AAAAAAAAAAAAAAA' as SEQ ID NO: 5.

---

SEQUENCE LISTING

<160> NUMBER OF SEQ ID NOS: 5

Figure 1:
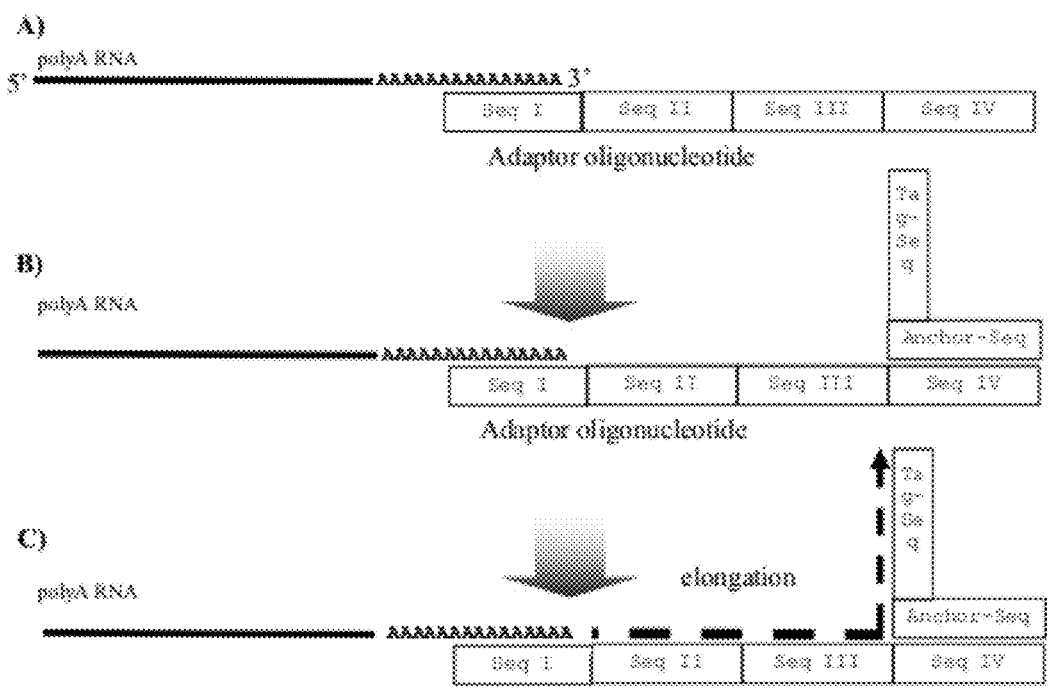
FIG. 1 illustrates one embodiment of the present invention. A) In a first step an adapter oligonucleotide probe (first nucleic acid probe) is hybridized to the poly A-tail of mRNA. B) In a second step the anchor oligonucleotide is hybridized to the adapter oligonucleotide. Note that in e preferred embodiment A) and B) occur simultaneously. C) The mRNA is elongated, adapter oligonucleotide and anchor oligonucleotide serve as a primer. The adaptor oligonucleotide comprises the following different sequence elements: Seq I: comprising a poly T or Poly-U stretch to bind to poly A-tail; Seq II: comprising a primer binding sequence; Seq III: comprising a probe binding sequence; Seq IV: comprising an anchor oligonucleotide binding sequence.
Figure 2:
FIG. 2 illustrates an embodiment of the anchor oligonucleotide with a 5' tag sequence (primer and/or probe binding sites) and a 3' prime binding site for the adapter oligonucleotide.

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cacatcagga ttcctaggac caatatcact cacc                                      34

<210> SEQ ID NO 2
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
ggtgagtgat tggagggttg agcacatcag agccctgcga tgagtctgtc gtcgtctcgt          60
tccauuuuuu uuuuuuuuuu                                                      80

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 3
aacgagacga cgacagac                                              18

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cacatcagga ttcctaggac c                                          21

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaaaaaaaaa aaaaa                                                 15
```

The invention claimed is:

1. A method for normalization of a quantity of a nucleic acid to be quantified in a sample to
   (i) a total quantity of nucleic acid in the sample; or to
   (ii) a total quantity of a specific class of nucleic acid in the sample, comprising the steps of
   (a) providing a sample containing a nucleic acid to be quantified;
   (b) adding a first nucleic acid probe to the sample under conditions allowing for hybridization of at least a terminal region of said first nucleic acid probe to specific binding sites of said nucleic acid in the sample such that double-stranded nucleic acids are created, wherein said first nucleic acid probe comprises at least one primer binding site, a probe binding site, and an anchor oligonucleotide binding site, and wherein said specific binding sites are a poly-A sequence, a poly-A tail, a poly-T-sequence or a poly-T-tail;
   (c) adding an anchor oligonucleotide under conditions allowing for hybridization to the anchor oligonucleotide binding site of the first nucleic acid probe so that a 5' sequence of the anchor oligonucleotide is not hybridized to the first nucleic acid probe;
   (d) elongating the nucleic acid at its 3' end, wherein said first nucleic acid probe serves as template until a region is reached where said anchor oligonucleotide is hybridized to the first nucleic acid probe whereon the anchor oligonucleotide serves as a template for further elongation;
   (e) quantifying the total quantity of nucleic acid in the sample or the total quantity of the specific class of nucleic acid in the sample using a second probe substantially complementary to a region of DNA transcribed from said first nucleic acid probe and said anchor oligonucleotide;
   (f) quantifying the nucleic acid to be quantified using optionally a third probe whose sequence is substantially identical to a defined region of the nucleic acid to be quantified; and
   (g) normalizing the quantity of the nucleic acid to be quantified by determining the ratio of the quantity of the nucleic acid to be quantified to the total quantity of nucleic acid in the sample or the total quantity of the specific class of nucleic acid in the sample.

2. The method according to claim 1, wherein the nucleic acid to be quantified is RNA and the specific class of nucleic acid is RNA.

3. The method according to claim 2, wherein the RNA to be quantified is RNA selected from the group consisting of mRNA, rRNA, tRNA, mRNA, siRNA, snRNA, snoRNA, scaRNA, microRNA, dsRNA, ribozyme, riboswitch and viral RNA and wherein the total quantity of RNA is selected from the group consisting of the total quantity of RNA, the total quantity of mRNA, the total quantity of rRNA, the total quantity of tRNA, the total quantity of nRNA, the total quantity of siRNA, the total quantity of snRNA, the total quantity of snoRNA, the total quantity of scaRNA, the total quantity of microRNA, the total quantity of dsRNA, the total quantity of ribozyme, the total quantity of riboswitch and the total quantity of viral RNA.

4. The method according to claim 3, wherein the RNA to be quantified is mRNA and the specific class of nucleic acid is mRNA.

5. The method according to claim 4, wherein the specific binding site is the poly-A sequence or the poly-A tail.

6. The method according to claim 5, wherein said first nucleic acid probe hybridizes in such a fashion to said specific binding site that it is positioned at or close to the 5' end of said poly-A sequence or poly-A tail.

7. The method according to claim 2, additionally comprising a step of contacting the RNA in the sample with a reverse transcriptase under conditions allowing for the reverse transcription of RNA or the specific class of RNA in the sample.

8. The method according to claim 2, additionally comprising a step of contacting the RNA in the sample with a reverse transcriptase subsequent to the ligation step under conditions allowing for the reverse transcription of RNA or the specific class of RNA in the sample.

9. The method according to claim 8, wherein the quantification comprises quantitative real-time reverse transcription PCR.

10. The method according to claim 8, wherein reverse transcribing and quantifying are performed in the same reaction container.

11. The method according to claim 1, wherein the nucleic acid to be quantified is DNA and the specific class of nucleic acid is DNA.

12. The method according to claim 11, wherein the DNA to be quantified is DNA selected from the group consisting of cDNA, dsDNA, ssDNA, plasmid DNA, cosmid DNA, chromosomal DNA, viral DNA and mtDNA and wherein the total quantity of DNA is selected from the group consisting of the total quantity of DNA, the total quantity of cDNA, the total quantity of dsDNA, the total quantity of ssDNA, the total quantity of plasmid DNA, the total quantity of cosmid DNA, the total quantity of chromosomal DNA, the total quantity of viral DNA and the total quantity of mtDNA.

13. The method according to claim 12, wherein the DNA to be quantified is cDNA and the specific class of nucleic acid is cDNA.

14. The method according to claim 13, wherein the specific binding site is the poly-T sequence or the poly-T tail.

15. The method according to claim 1, wherein the first nucleic acid probe is DNA or RNA.

16. The method according to claim 1, wherein quantification comprises quantitative real-time PCR.

17. The method according to claim 1, wherein the quantification comprises quantitative real-time PCR.

18. The method according to claim 1, wherein the second and third nucleic acid probe are labelled with one or more fluorescent dye(s) and wherein the quantifying steps comprise detecting fluorescence signals in the sample.

19. The method according to claim 1, wherein additionally a pre-quantified nucleic acid is added to the sample and wherein the quantity of said pre-quantified nucleic acid is determined in the quantifying steps.

20. A method for normalization of a quantity of a nucleic acid to be quantified in a sample to
  (i) a quantity of a reference nucleic acid,
  comprising the steps of,
  (a) providing a sample containing a nucleic acid to be quantified;
  (b) adding a first nucleic acid probe to the sample under conditions allowing for hybridization of at least a terminal region of said first nucleic acid probe to specific binding sites of said nucleic acid in the sample such that double-stranded nucleic acids are created, wherein said first nucleic acid probe comprises at least one primer binding site, a probe binding site and an anchor oligonucleotide binding site, and wherein said specific binding sites are a poly-A-sequence, a poly-A-tail, a poly-T-sequence or a poly-T-tail;
  (c) adding an anchor oligonucleotide under conditions allowing for hybridization to the anchor oligonucleotide binding site of the first nucleic acid probe so that a 5' sequence of the anchor oligonucleotide is not hybridized to the first nucleic acid probe;
  (d) elongating the nucleic acid at its 3' end, wherein said first nucleic acid probe serves as template until a region is reached where said anchor oligonucleotide is hybridized to the first nucleic acid probe whereon the anchor oligonucleotide serves as a template for further elongation;
  (e) quantifying the quantity of the reference nucleic acid using a second probe substantially complementary to a region of the DNA transcribed from said first nucleic acid probe and said anchor oligonucleotide;
  (f) quantifying the nucleic acid to be quantified using optionally a third probe whose sequence is substantially identical to a defined region of the nucleic acid to be quantified; and
  (g) normalizing the quantity of the nucleic acid to be quantified by determining the ratio of the quantity of the nucleic acid to be quantified to the quantity of nucleic acid in the reference nucleic acid.

21. A method for the quantification of gene expression levels in a sample by normalization of a quantity of nucleic acid to
  (i) a total quantity of nucleic acid in the sample; or to
  (ii) a total quantity of a specific class of nucleic acid in the sample,
  comprising the steps of
  (a) providing a sample containing a gene to be quantified;
  (b) adding a first nucleic acid probe to the sample under conditions allowing for hybridization of at least a terminal region of said first nucleic acid probe to specific binding sites of said nucleic acid in the sample such that double-stranded nucleic acids are created, wherein said first nucleic acid probe comprises at least one primer binding site, a probe binding site, and an anchor oligonucleotide binding site, and wherein said specific binding sites are a poly-A sequence, a poly-A-tail, a poly-T-sequence or a poly-T-tail;
  (c) adding an anchor oligonucleotide under conditions allowing for hybridization to the anchor oligonucleotide binding site of the first nucleic acid probe so that a 5' sequence of the anchor oligonucleotide is not hybridized to the first nucleic acid probe;
  (d) elongating the nucleic acid at its 3' end, wherein said first nucleic acid probe serves as template until a region is reached where said anchor oligonucleotide is hybridized to the first nucleic acid probe whereon the anchor oligonucleotide serves as a template for further elongation;
  (e) quantifying the total quantity of nucleic acid in the sample or the total quantity of the specific class of nucleic acid in the sample using a second probe substantially complementary to a region of the DNA transcribed from said first nucleic acid probe and said anchor oligonucleotide;
  (f) quantifying the nucleic acid to be quantified using optionally a third probe whose sequence is substantially identical to a defined region of the nucleic acid to be quantified; and
  (g) normalizing the quantity of the nucleic acid of the gene to be quantified by determining the ratio of the quantity of the nucleic acid to be quantified to the total quantity of nucleic acid in the sample or the total quantity of the specific class of nucleic acid in the sample.

* * * * *